United States Patent [19]
Abell et al.

[11] Patent Number: 5,863,776
[45] Date of Patent: *Jan. 26, 1999

[54] METHOD OF PREPARING APOENZYME

[75] Inventors: Creed W. Abell; Sau-Wah Kwan, both of Austin; Binhua Zhou, Houston; Duane A. Lewis, Big Spring, all of Tex.

[73] Assignee: Research Development Foundation, Carson City, Nev.

[*] Notice: This patent issued on a continued prosecution application filed under 37 CFR 1.53(d), and is subject to the twenty year patent term provisions of 35 U.S.C. 154(a)(2).

[21] Appl. No.: 714,922

[22] Filed: Sep. 17, 1996

Related U.S. Application Data

[60] Provisional application No. 60/003,921 Sep. 18, 1995.

[51] Int. Cl.[6] ........................................... C12N 9/02
[52] U.S. Cl. ............... 435/189; 435/325; 435/172.3; 536/23.2; 536/23.5
[58] Field of Search ................. 435/189, 240.2, 435/172.3, 325

[56] References Cited

PUBLICATIONS

Brandsch et al. "Autoflavinylation of apo6–hydroxy–D–nicotine oxidase" J. Biol. Chem. 266, 19056–19062, Oct. 1991.

Brandsch et al. "Studies in vitro on flavinylation of 6–hydroxy–D–nicotine oxidase" Eur. J. Biochem. 160, 285–289 1986.

Zhou et al. "Mutagensis at highly conserved tyrosine in monoamine oxidase B affects FDA . . . " Biochemistry 34, 9526–9531, Jul. 25, 1995.

Lan et al. "Expression of functional human monoamine oxidase A and B cDNA in mammalian cells" J. Neurochem. 52, 1652–1654, 1989.

Wu et al. "Site–directed mutagensis of monoamine oxidase A and B: Role of cysteines" Mol. Pharm. 43, 888–893, Jun. 1993.

Gluzman, Y. "SV40–transformed simian cells support the replication of early SV40 mutants" Cell 23, 175–182, Jan. 1981.

Bach et al. "cDNA cloning of human liver monoamine oxidase A and B: molecular basis of differences in enzymatic properties" Proc. Natl. Acad. Sci. USA 85, 4934–4938, Jul. 1988.

Potter et al. "Enhancer–dependent expression of human k immunoglobulin genes . . . by electroporation" Proc. Natl. Acad. Sci. USA 81, 7161–7165, Nov. 1984.

*Primary Examiner*—Robert A. Wax
*Assistant Examiner*—Nashaat T. Nashed
*Attorney, Agent, or Firm*—Benjamin Aaron Adler

[57] ABSTRACT

The present invention provides a method of preparing apoenzyme of a riboflavin-dependent enzyme, comprising the steps of: growing COS-7 cells in a riboflavin-free medium; introducing a cDNA encoding a riboflavin-dependent enzyme; and expressing said cDNA. Also provided is a method of screening for an inhibitor of a flavin dependent enzyme, comprising the steps of;

contracting a potential inhibitor of a flavin dependent enzyme with the cell line of claim 7 in the presence of riboflavin, FMN or Fad; and measuring the enzymatic activity of the flavin dependent enzyme.

4 Claims, 8 Drawing Sheets

METHOD OF PREPARING APOENZYME

This is a continuation of provisional application Ser. No. 60/003,921, filed Sep. 18, 1995.

BACKGROUND OF THE INVENTION

1. Field of the Invention

The present invention relates generally to the fields of immunology and protein chemistry. More specifically, the present invention relates to a novel cell system and methods of preparing apoenzyme.

2. Description of the Related Art

The major amine-degrading enzymes in the central nervous system and peripheral tissues of mammals are monoamine oxidase A and B [MAO A and B; amine: oxygen, oxidoreductase (deaminating, flavin-containing), EC 1.4.3.4]. These isozymes are integral proteins of the outer mitochondrial membrane (1) and can be distinguished by differences in substrate preference (2), inhibitory specificity (3), tissue and cell distribution (4–6), and immunological properties (7–9). Furthermore, comparison of their nucleotide and deduced amino acid sequences show that human MAO A and B are two distinct proteins encoded by different genes (10).

Oxidation of amines by MAO is coupled to the reduction of an obligatory cofactor, FAD, which is covalently linked to the enzyme. Five types of bonds are generally found in the covalent linkage of flavins to their respective apoproteins (11). These include a histidine residue which can be attached through its N-1 or N-3 atom to the 8α-methyl group of the isoalloxazine ring to form a tertiary amine; a cysteine residue which forms a thioether linkage with either the 8α-methyl group or the C-6 of the xylene ring of the flavin molecule; or a tyrosine residue can become linked to the 8α-methyl group to form an (O)-8α-flavin bond. In MAO A and B, the 8α-methyl group of FAD is bound covalently to cysteine through a thioether linkage in the pentapeptide SGGCY (12, 13). Comparison of this segment with the complete deduced amino acid sequences of MAO A and B indicated that FAD is covalently bound to $Cys^{406}$ in MAO A and $Cys^{397}$ in MAO B, respectively (10). In addition, site-directed mutagenesis studies of MAO B, where $Cys^{397}$ was substituted with serine or histidine, showed that this cysteine residue is essential for catalytic activity (14, 15).

Although the amino acid sequences surrounding the FAD covalent attachment site in different flavoproteins bear little homology, a distinct non-covalent FAD binding site displays high sequence identity in many FAD-containing enzymes of diverse function (16, 17). This non-covalent FAD binding region is commonly referred to as the dinucleotide binding site or motif due to its interaction with the AMP moiety of FAD. This motif consists of a $\beta_1$ sheet-α helix-$\beta_2$ sheet beginning with a highly conserved Gly-X-Gly-X-X-Gly sequence between the first β-sheet and the α-helix. The second β-sheet usually ends with a glutamate residue in which the γ-carboxylate group is thought to interact through a hydrogen bond with the 2'-hydroxyl group of ribose in the AMP moiety of FAD. In MAO A and B, this motif is located at the N-terminus of MAO A (residues 15–43) and MAO B (residues 6–34), and ends in $Glu^{43}$ and $Glu^{34}$, respectively. Site-directed mutagenesis studies, where $Glu^{34}$ was replaced with aspartate, glutamine or alanine, resulted in near complete or total loss of catalytic activity in MAO B (18).

A fundamental process in the intracellular generation of functional flavoenzymes is the molecular mechanism which generates holoenzyme from apoenzyme and its cofactor. Following the discovery of the first known enzyme with covalently linked FAD (succinate dehydrogenase, 19), extensive research in many laboratories has been conducted to elucidate how FAD is coupled to its respective proteins. The precise steps involved remain unknown.

The prior art is deficient in the lack of effective means of manipulating the flavinylation of enzymes and the preparation of apoenzymes. The present invention fulfills this longstanding need and desire in the art.

SUMMARY OF THE INVENTION

The present invention has developed a novel riboflavin-depleted (Rib⁻) COS-7 cell line to manipulate the flavinylation of MAO B. Apo-MAO B was obtained by expressing MAO B cDNA in these cells. The expression of MAO B apoenzyme is independent of FAD and that apo-MAO B can be inserted into the outer mitochondrial membrane. Coupling of flavin to the apoenzyme was studied using FAD, flavin derivatives, or [$^{14}$C] FAD. The role of a critical glutamate residue ($Glu^{34}$) in flavinylation of MAO B was also examined using site-directed mutants. $Glu^{34}$ plays an essential role in flavin coupling to the apoenzyme. The dinucleotide-binding site at the N-terminus of MAO B provides a topological dock for the inital binding of FAD, and then FAD is delivered to the covalent attachment site at $Cys^{397}$.

Monoamine oxidase B (MAO B) catalyzes the oxidative deamination of biogenic and xenobiotic amines. The oxidative step is coupled to the reduction of an obligatory cofactor, FAD, which is covalently linked to the enzyme at $Cys^{397}$. In the present invention, a novel riboflavin-depleted (Rib⁻) COS-7 cell line was developed to illustrate the flavinylation of MAO B. Apo-MAO B was obtained by expressing MAO B cDNA in these cells. MAO B was expressed equally in the presence or absence of FAD, and apo-MAO B can be inserted into the outer mitochondrial membrane. Flavinylation of MAO B was achieved by introducing MAO B cDNA and different flavin derivatives simultanously into Rib⁻ COS-7 cells via electroporation. Since the addition of riboflavin, FMN or FAD resulted in equal levels of MAO B activity, it was apparent that the flavin which initially binds to apo-MAO B is FAD. Site-directed mutagenesis has shown that $Glu^{34}$ in the dinucleotide-binding motif of MAO B is essential for MAO B activity and that this residue is involved in FAD binding. The present invention showed the role of residue 34 in flavin binding by expressing wild-type or mutant MAO B cDNA in Rib⁻ COS-7 cells with the addition of [$^{14}$C] FAD. $Glu^{34}$ is essential for both FAD binding and catalytic activity. Thus, FAD binds to MAO B in a dual manner at $Glu^{34}$ noncovalently and $Cys^{397}$ covalently. $Glu^{34}$ is critical for the initial non-covalent binding of FAD and is instrumental in delivering FAD to the covalent attachment site at $Cys^{397}$.

In one embodiment of the present invention, there is provided a composition of matter comprising a novel cell line useful for preparing apoenzymes.

In another embodiment of the present invention, there is provided a method of preparing an apoenzyme as described herein. For example, the present invention provides a method of preparing apoenzyme of a riboflavin-dependent enzyme, comprising the steps of growing cells suitable for expression of proteins in a riboflavin-free medium; introducing a cDNA encoding a riboflavin-dependent enzyme; and expressing said cDNA.

In another embodiment of the present invention, there is provided a novel riboflavin-depleted ("Rib") COS-7 cell line, said cell line useful for preparing apoenzyme and prepared by a method comprising the steps of:

growing COS-7 cells in a riboflavin free medium until said cells are riboflavin depleted;

introducing into said cells a cDNA that encodes a flavin dependent enzyme and expressing said cDNA.

In another embodiment of the present invention, there is provided a method of screening for an inhibitor of a flavin dependent enzyme, comprising the steps:

contacting a potential inhibitor of a flavin dependent enzyme with the cell line of claim 7 in the presence of riboflavin, FMN or FAD; and measuring the enzymatic activity of the flavin dependent enzyme.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1A:
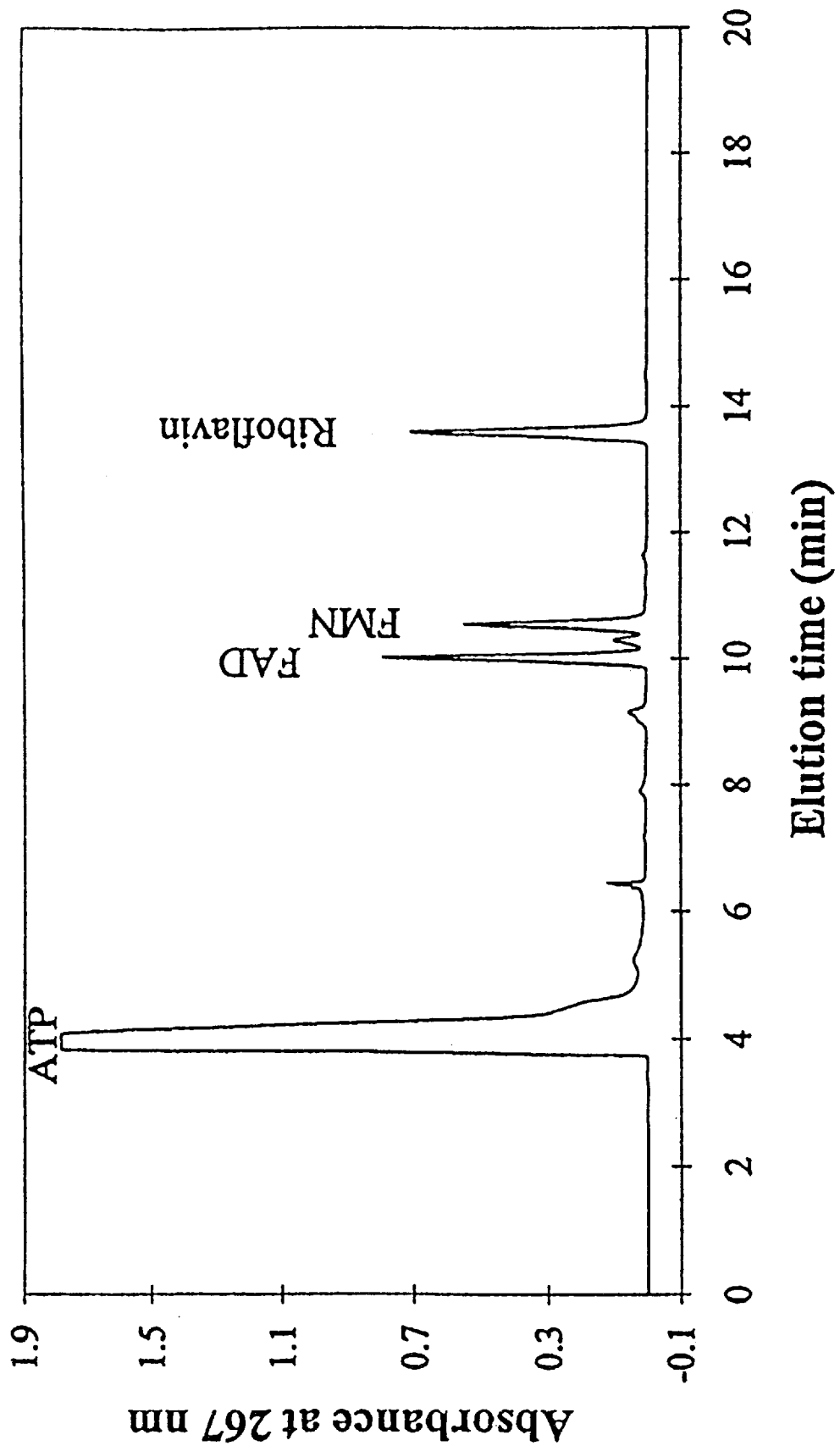
FIG. 1A shows the elution chromatogram of standards. Pure ATP, FAD, FMN and riboflavin (Sigma) were eluted on a C-18 Semi-Prep column with a linear gradient from 100% A/0% B (A=10 mM $(NH_4)_2HPO_4$, pH 6.8; B=acetonitrile) to 60% A/40% B in 20 min at a flow rate of 4 ml/min. The FAD standard was eluted at a retention time of 10 min.

In the present invention, a procedure has been developed to assess flavinylation, i.e., FAD covalent binding, of MAO B in mammalian cells. FAD is an obligatory cofactor which binds either non-covalently or covalently in a wide variety of flavoproteins that are involved in oxidation and reduction, electron transport, DNA repair and catabolism of neurotransmitters. The novel methods of the present invention are applicable to any of the proteins that contain covalently bound FAD.

Basically, in one embodiment of the present invention, COS-7 cells are grown in riboflavin free medium for greater that 120 days. The cells are then isolated and the cDNA that encodes MAO B is introduced into the cells by one of various methods known in the art, such as electroporation. The cDNA is introduced either in the absence of riboflavin, FMN or FAD to yield apoenzyme (inactive enzyme) or in the presence of riboflavin, FMN or FAD to yield holoenzyme (active enzyme). Thus, potential inhibitors of enzymatic activity can be readily surveyed by adding the drug with FAD.

The novel cell systems and methods of the present invention have several unique features. First of all, COS-7 cells have the capacity to grow in the absence of riboflavin at approximately the same rate as those cells that are maintained in medium containing riboflavin. This finding is unexpected because riboflavin is an essential vitamin that cannot be synthesized by mammals. Presumably, COS-7 cells have the ability to utilize trace amounts of riboflavin for essential physiological processes. COS-7 cells are African green monkey cells that have been transformed with SV40 virus and are readily available from the ATCC. The riboflavin free medium is obtained from GIBCO.

Further, in another embodiment of the present invention, one with ordinary skill in the art can prepare apoenzyme of an enzyme that binds to FAD covalently. Thus, a method is provided to screen for any riboflavin derivative (or other compounds designed by computer assistance) that is postulated to inhibit enzymatic activity. Thus, it is possible to apply the technology disclosed by the present invention to any enzyme that covalently binds to FAD, of which there are presently at least thirteen known.

The present invention provides a methods of preparing apoenzyme of a riboflavin-dependent enzyme, comprising the steps of growing cells suitable for expression of proteins in a riboflavin-free medium; introducing a cDNA encoding a riboflavin-dependent enzyme into said cells; and expressing said cDNA.

According to this method of the present invention, the apoenzyme of any riboflavin-dependent enzyme may be prepared. In a preferred embodiment, the apoenzyme is a monoamine oxidase.

According to this method of the present invention, the cDNA may be introduced by any method well known to those having ordinary skill in this art. Preferably, the introducing is by transfection of the cells with a cDNA encoding a riboflavin-dependent enzyme or by electroporation. The present invention also provides an apoenzyme prepared by this method of the present invention.

The present invention also provides a novel riboflavin-depleted ("RIB") COS-7 cell line, said cell line is useful for preparing apoenzymes. In a preferred embodiment, the novel riboflavin-depleted ("RIB") COS-7 cell line is prepared by a method comprising the steps of:

growing COS-7 cells in a riboflavin free medium until said cells are riboflavin depleted;

introducing into said cells cDNA that encodes a flavin dependent enzyme; and expressing said cDNA. Preferably, the COS-7 cells are grown in a riboflavin free medium for about 120 days. Although any flavin dependent enzyme may be prepared according to this method, a preferred enzyme is MAO B.

The present invention also provides a novel method of screening for an inhibitor of a flavin dependent enzyme, comprising the steps of contracting a potential inhibitor of a flavin dependent enzyme with the cell line of claim 7 in the presence of riboflavin, FMN or FAD; and measuring the enzymatic activity of the flavin dependent enzyme. As will be readily apparent to one having ordinary skill in this art, an inhibitor of a flavin dependent enzyme can be determined using this novel screening method. A preferred inhibitor of a flavin dependent enzyme is an inhibitor of monoamine oxidase B.

The following examples are given for the purpose of illustrating various embodiments of the invention and are not meant to limit the present invention in any fashion.

EXAMPLE 1
Synthesis of $[^{14}C]$ FAD $[^{14}C]$ FAD was prepared by a modified method of Manstein and Pai(20). The reaction mixture (530 ml) contained 15 mM $MgCl_2$, 6.5 mM ATP, 0.12 mM $[^{14}C]$ riboflavin (Amersham, 50 mCi/mmol) and 200 μg of FAD synthetase (purified from *Brevibacterium ammoniagenes*). After incubation at 37° C. for 20 hours, the mixture was filtered through a 100,000 MW cut-off spin filter (Millipore) to remove the insoluble components. The clear yellow solution was loaded on a C-18 Semi-Prep HPLC column (Beckman), and eluted with a linear gradient from 100% A/0% B (A=10 mM $(NH_4)_2HPO_4$, pH 6.8; B=acetonitrile) to 60% A/40% B in 20 minutes at a flow rate of 4 ml/minute using a Beckman HPLC (System Gold). The peak corresponding to $[^{14}C]$ FAD eluted at a retention time identical to an FAD standard (Sigma). $[^{14}C]$ FAD was collected in sterilized silicone coated glass tubes, dried in a Beckman speedvac, and stored at −20° C. in powder form.

EXAMPLE 2
Synthesis of 8α-Hydroxyriboflavin

Synthesis of 8α-hydroxyriboflavin was carried out by the method of McCormick (21). Briefly, riboflavin was added to a solution of acetic acid: acetic anhydride (1:1) and the yellow solution was stirred at room temperature for 24 hours. Tetra-acetylriboflavin (TAR) was extracted from the aqueous reaction mixture with $CHCl_3$, followed by extraction with water and evaporation to give a yellow residue of essentially pure TAR. Dibenzoyl peroxide and dioxane dibromide in dioxane were added to a solution of TAR in dioxane, and the solution was refluxed. The crude bromo-TAR was separated from the reaction mixture on a C-18 Semi-Prep HPLC column (Beckman). The bromo-TAR was hydrolyzed to yield 8α-hydroxyriboflavin, which was separated by HPLC (System Gold, Beckman) through a linear gradient from 0.5% trifluoroacetic acid (TFA) in water to 0.5% TFA in acetonitrile for 50 minutes at a flow rate of 4 ml/minute.

EXAMPLE 3
Cell Culture

Mammalian COS-7 cells were selected for transient expression of MAO B cDNA because they were found to contain no endogenous MAO B, as determined by ELISA, Western blot, and radiometric activity assays in initial experiments. Mammalian COS-7 cells were grown in Dulbecco's Modified Eagle Medium (DMEM, Gibco) supplemented with 10% fetal bovine serum (FBS, Gibco) at 37° C. with 5% $CO_2$. Since this medium (DMEM+10% FBS) contains riboflavin, COS-7 cells grown in this medium were defined as riboflavin-containing COS-7 cells ($Rib^+$ COS-7 cells). MAO B holoenzyme was obtained by expressing MAO B cDNA in $Rib^+$ COS-7 cells. Mammalian COS-7 cells were also grown in riboflavin-free medium (riboflavin-free DMEM+10% dialyzed FBS, Gibco) at 37° C. with 5% $CO_2$, with fresh riboflavin-free medium changed every 48–72 hours. COS-7 cells grown in riboflavin-free medium for longer than 100 days were defined as riboflavin-depleted ($Rib^-$) COS-7 cells. Apo-MAO B was obtained by expressing MAO B cDNA in $Rib^-$ COS-7 cells. COS-7 cells were grown in riboflavin-free medium for greater than 5 months without any detectable change in morphology.

EXAMPLE 4
Preparation of Mutant MAO B cDNA

Mutagenesis was carried out by the method of Deng and Nickoloff (22) using a Transformer Site-directed Mutagenesis kit (Clontech). Glu in position 34 was replaced with Asp (E34D), Gln (E34Q), or Ala (E34A), and Val in position 10 was replaced with Ile (V10I) as described by Kwan et al. (18).

EXAMPLE 5
FAD coupling in intact cells

Wild-type or mutant MAO B cDNAs were transiently transfected into COS-7 cells by electroporation (23) as previously described (18). Briefly, Rib$^+$- or Rib$^-$ COS-7 cells were harvested during late log phase growth and resuspended to a concentration of $3.1 \times 10^6$ cells/ml in either riboflavin-containing or riboflavin-free medium, respectively. Wild-type or mutant MAO B cDNAs (15 mg) were added to 0.8 ml of cell suspension. In experiments where flavinylation of wild-type and variant MAO B enzymes were studied, 20 µl of 0.8 mM unlabeled FAD, [$^{14}$C] FAD or other flavin derivatives were also added to the Rib$^-$ COS-7 cell suspension. Electroporation was carried out in a Bio-Rad Gene Pulser with a setting of 250 V and 500 µF. Cells were resuspended in 15 ml of riboflavin-containing or riboflavin-free medium and incubated at 37° C. with 5% $CO_2$. Transfected COS-7 cells were harvested at 48 hours and homogenized in a lysis solution containing 20 mM Tris-HCl, 1 mM EDTA, 0.5 mM PMSF, pH 8.0. The homogenate was diluted with an equal volume of the same buffer supplemented with 300 mM NaCl to obtain a 150 mM final NaCl concentration. Triton X-100 (Pierce) was added to the lysate to give a final concentration of 0.25%, and the samples were allowed to stir for 50 min. at 4° C. to extract MAO B from the outer mitochondrial membrane. After Triton extraction, the lysate was centrifuged at 1300×g for 5 min. at 4° C. to remove insoluble cell debris. The supernatant was then analyzed for protein concentration, MAO B concentration, enzymatic activity, and FAD coupling.

EXAMPLE 6
FAD coupling in vitro

Apo-MAO B was obtained by expressing MAO B cDNA in Rib$^-$ COS-7 cells. The cells were then harvested and homogenized as described above. One half of the lysate was stirred in the presence of 0.25% Triton X-100 at 4° C. for 50 min. to extract apo-MAO B from the outer mitochondrial membrane. The second half of the lysate was not extracted with Triton X-100 to permit MAO B to remain in the membrane. FAD coupling assays were carried out for both fractions in reaction vials (200 µl) containing 10 µl of cell lysate, 50 mM phosphate buffer and FAD (1.5 nmoles). Assays were also carried out in the presence of an energy mixture (10 mM ATP, 32 mM PEP and 2.4 µg pyruvate kinase) and 25% glycerol in the reaction vials. Each sample was run in triplicate. After 1, 2 or 3 hours incubation at 30° C., each sample was assayed for MAO B activity as described below.

EXAMPLE 7
Subcellular fractionation of COS-7 Cells

COS-7 subcellular fractionation was carried out with a modified method of Clark and Waterman (24). Transfected Rib$^+$- or Rib$^-$ COS-7 cells were harvested, washed twice with ice-cold PBS, and pelleted by microcentrifugation at 500×g for 5 minutes. The cells were then homogenized in a Dounce homogenizer. Greater than 95% of the cells were lysed, as determined by trypan blue staining. The homogenate was diluted with an equal volume of 10 mM Tris-HCl, 1 mM EDTA, pH 8.0, to obtain a 0.25M final sucrose concentration and layered over 0.5 volume of 0.5M sucrose pad (0.5M sucrose in 10 mM Tris-HCl, 1 mM EDTA, pH 8.0). The solution was centrifuged at 5,000 rpm for 3 minutes using a swinging bucket rotor (TLS.55, Beckman TL-100) to remove cell debris and nuclei ($P_1$ fraction). The supernatant plus the interface of the 0.5M sucrose pad was again layered over another 0.5M sucrose pad, and centrifuged as above at 17,000 rpm for 20 minutes to isolate mitochondria ($P_2$ fraction). The resulting supernatant was centrifuged at 70,000 rpm (TL100.3, Beckman TL-100) for 30 minutes to sediment microsomes ($P_3$ fraction). The final supernatant was the cytosol (S). After subcellular fractionation, $P_1$, $P_2$ and $P_3$ were resuspended in 20 mM Tris-HCl, 1 mM EDTA, 0.5 mM PMSF, 150 mM NaCl, pH 8.0. All samples were treated with Triton X-100 to extract MAO B, and then protein concentrations, MAO B concentrations and enzymatic activities were determined.

EXAMPLE 8
Quantitation of MAO B protein

Total protein concentrations of samples containing MAO B holoenzyme, apoenzyme, or variant MAO Bs were determined by a MicroBCA kit (Pierce). All samples were then adjusted to equal protein concentrations and assayed for MAO B protein by ELISA using a modification of the method of Yeomanson and Billett (25) as described previously (18).

EXAMPLE 9
Enzyme Activity Determination

MAO B activity was assayed radiometrically by a modification of the method of Wurtman and Axelrod (26) as described previously (18). Briefly, the reaction mixture contained 200 µl of 50 mM sodium phosphate buffer (pH 7.4), 3.6 nmole of 55 mCi/mmol [$^{14}$C] benzylamine hydrochloride (Amersham), 10 nmoles of unlabeled benzylamine and 10 µl of cell lysate. Samples were run in triplicate, and one out of each set was denatured with 25 ml of 6N HCl prior to the addition of substrate to serve as an internal control. All reactions were incubated for 9 minutes at 37° C., and terminated by the addition of 25 µl of 6N HCl. The reaction product was extracted with 500 µl of toluene, and an aliquot (200 µl) of the organic phase from each sample was counted in liquid scintillation fluid (Bio-Safe) in a Beckman LB 3801 scintillation counter.

EXAMPLE 10
Immunoprecipitation of Holo-, Apo- or Variant MAO B

Transfected Rib$^+$- or Rib$^-$ COS-7 cells were homogenized, and extracted with 0.25% Triton X-100 for 50 minutes at 4° C. The cell lysates were centrifuged at 1300×g for 5 minutes, and an aliqout of each supernatant was analyzed for MAO B concentration by ELISA. All supernatants were then adjusted to equal MAO B concentration and incubated with polyclonal goat anti-MAO B antibody (10 µg) overnight at 4° C. Protein-G Sepharose beads (Pierce) were added (50 µl) and incubation was continued for 3 hours. The protein-G Sepharose/goat antibody/MAO B immmunocomplex was collected by centrifugation at 10,000×g for 20 seconds and washed 6 times with 150 µl of 20 mM Tris buffer, pH 8.0. The immunocomplex was then dissolved in SDS-PAGE sample buffer and analyzed by Western blot or fluorography.

EXAMPLE 11
Western Blot Analysis and Fluorography

The immunoprecipitated proteins (obtained as described above) were subjected to electrophoresis in a 10% SDS-polyacrylamide gel and examined by Western blotting as previously described (18). The immunoprecipitated proteins (obtained as described above) were subjected to electrophoresis in a 10% SDS-polyacrylamide gel. The SDS-PAGE gel was fixed by soaking in 7% acetic acid, 10% methanol, 83% $H_2O$ for 1 hour, and then processed for fluorography as described by Bonner and Laskey (27). The dried gel was exposed to Kodak X-OMAT AR film at −80° C. for 2 weeks.

EXAMPLE 12
Synthesis of [$^{14}$C]FAD and 8α-hydroxyriboflavin

Figure 1B:
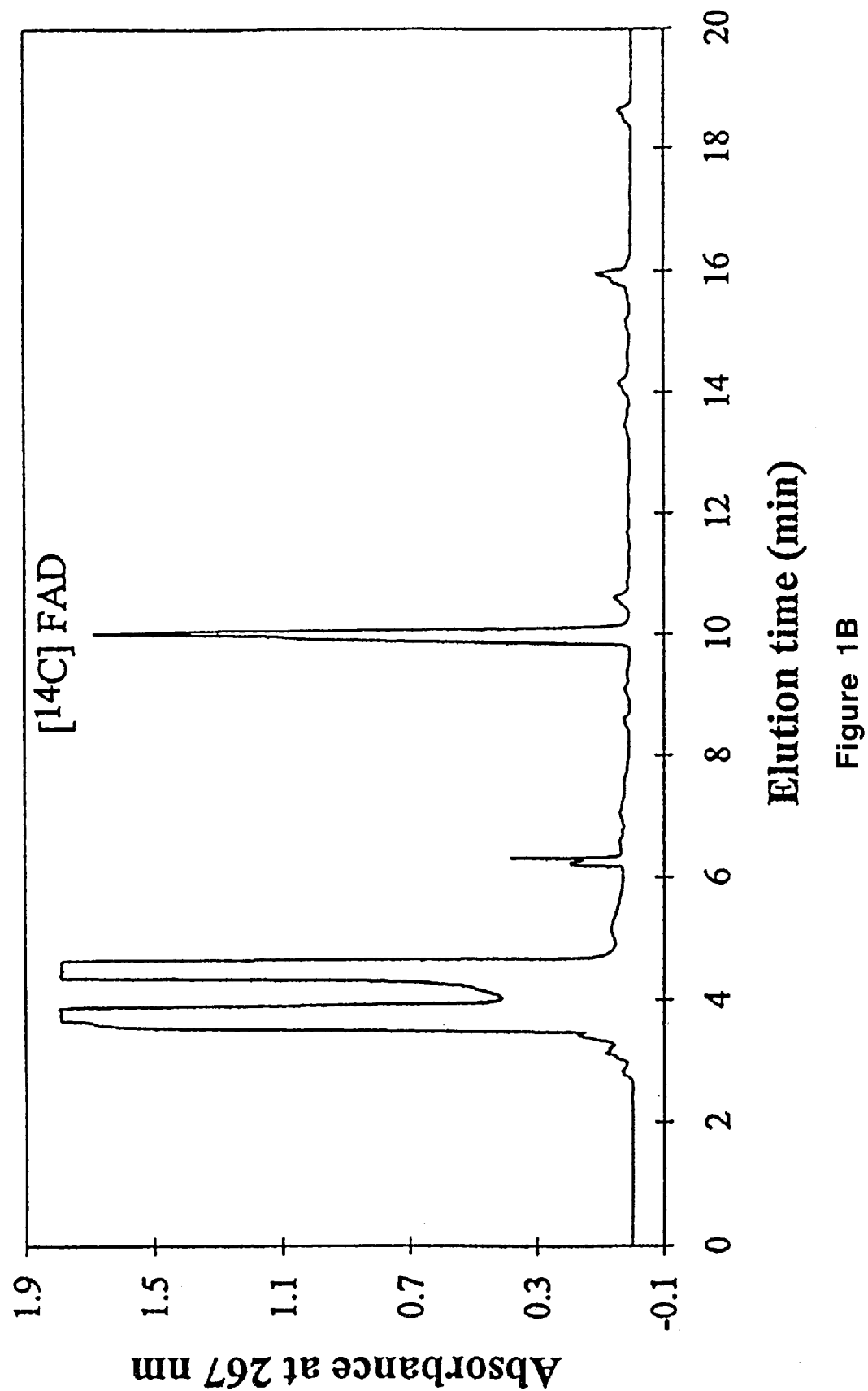
FIG. 1B shows an elution chromatogram of [$^{14}$C] FAD. The [$^{14}$C] FAD peak eluted at a retention time of 10 min using the same elution profile as above.

Retention times of riboflavin, FMN, FAD and ATP standards (Sigma) were determined (FIG. 1A). FAD was observed to have a retention time of 10 minutes. Synthetic [$^{14}$C] FAD had an identical retention time of 10 minutes (FIG. 1B), and eluted as a large sharp single peak. The radioactivity of the [$^{14}$C] FAD-containing fraction was determined in a scintillation counter and the sample was dried to obtain a fine yellow powder.

Figure 1C:
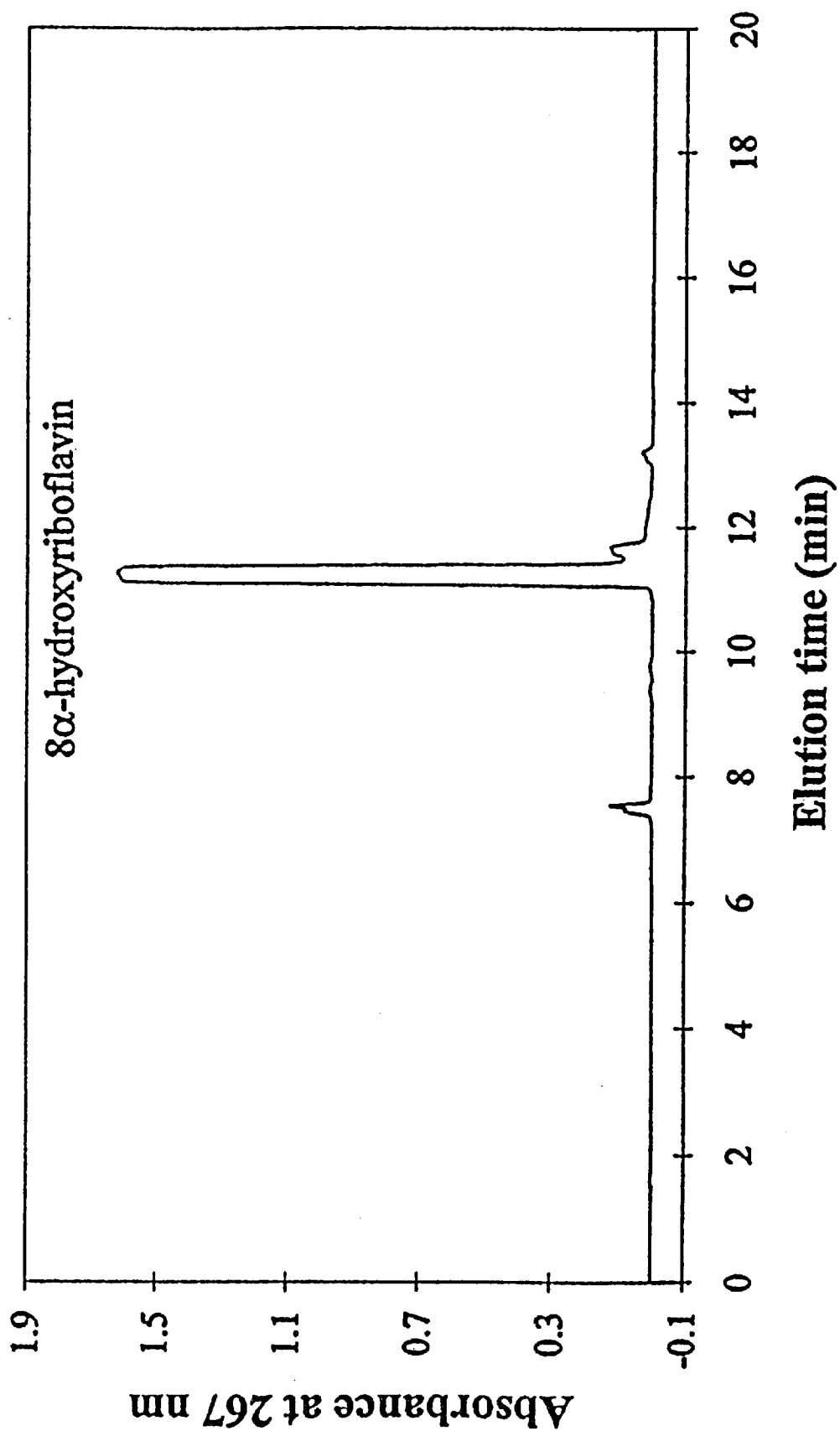
FIG. 1C shows an elution chromatogram of 8α-hydroxyriboflavin. Synthetic 8α-hydroxyriboflavin was isolated from the reaction mixture (see below), and rerun on high pressure liquid chromatography (HPLC) using the same elution conditions as above. 8α-hydroxyriboflavin gave a single sharp peak shown on the chromatogram. The authenticity of 8α-hydroxyriboflavin was confirmed by spectroscopic analysis (UV and Mass Spectrometry).

Synthesis of 8α-hydroxyriboflavin was carried out by the method of McCormick (21). Synthetic 8α-hydroxyriboflavin was resolved on HPLC to yield a major sharp peak on the chromatogram (FIG. 1C). The authenticity of 8α-hydroxyriboflavin was further confirmed by spectroscopic analysis (UV and mass spectrometry).

EXAMPLE 13
MAO B expression is independent of FAD cofactor

Figure 2:
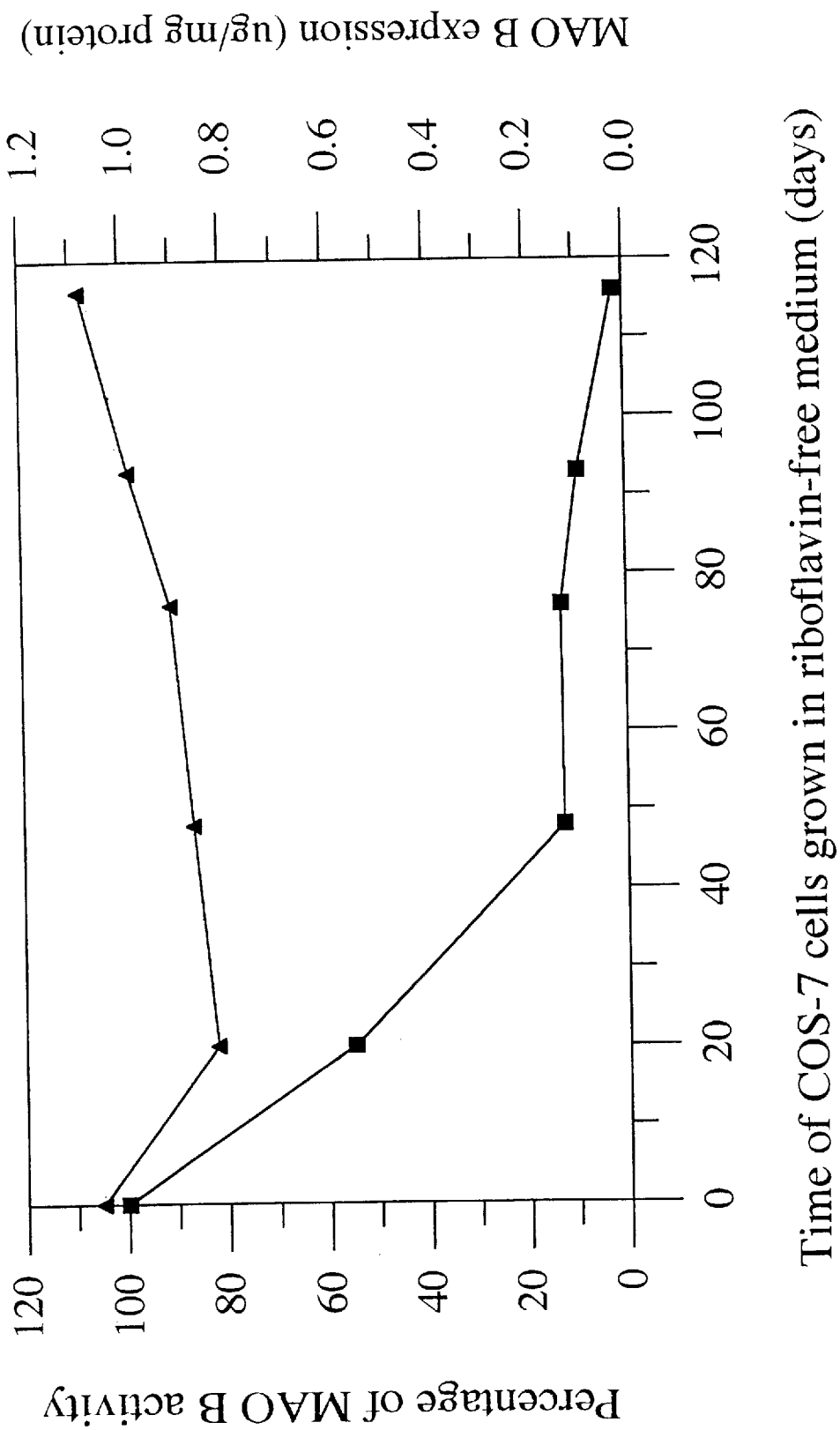
FIG. 2 shows the effect of riboflavin depletion in COS-7 cells on MAO B enzymatic activity and MAO B expression. MAO B cDNA was transfected into COS-7 cells at different time intervals during the process of riboflavin depletion from the cells. The expression level (filled triangles) and the MAO B activity (filled squares) from these cells were determined. The activity was expressed as the percentage of the enzymatic activity of MAO B holoenzyme obtained in Rib$^+$ COS-7 cells.

In order to examine the covalent binding of FAD to human MAO B, it was necessary to develop a method for obtaining apo-MAO B. To accomplish this, mammalian COS-7 (Rib$^+$) cells were grown in riboflavin-free medium to deplete the endogenous riboflavin. MAO B cDNA was expressed sequentially at different time intervals in these cells during this riboflavin depletion process (FIG. 2). Each data point in FIG. 2 represents an individual expression assay. For each assay, a sample of COS-7 cells grown in riboflavin-free medium were transfected with MAO B cDNA via electroporation. Concurrently, Rib$^+$ COS-7 cells were transfected with MAO B cDNA to serve as a control. Following incubation for 48 hours, the cells were homogenized and assays were performed to determine protein concentration, MAO B concentration by ELISA using polyclonal antibodies, and MAO B activity using [$^{14}$C] benzylamine. TABLE I shows one set of analyses performed on these COS-7 cells that had been grown in riboflavin-free medium for 76 days (point 4 in FIG. 2). The enzymatic activity of MAO B expressed in these cells was 12.7% of the control, while the level of expression was essentially identical to the control (0.90 μg MAO B/mg protein vs. 0.86 μg MAO B/mg protein).

TABLE I

Comparison of MAO B enzymatic activity and MAO B expression in Rib$^+$ COS-7 cells and COS-7 cells grown in riboflavin-free medium for 76 days

|  | Rib$^+$ COS-7 | Rib$^-$ COS-7 |
|---|---|---|
| [Protein] (mg/ml) | 4.09 | 4.09 |
| [MAO B] (μg/ml) | 3.50 | 3.70 |
| Expression (μg MAO B/mg prot.) | 0.86 | 0.90 |
| Enzymatic activity (μmol/minute/mg MAO B)[1] | 1.10 | 0.14 |
| % of holo-MAO B enzymatic activity | 100 | 12.7 |

An equal amount of MAO B cDNA (15 μg) was expressed in both types of cells (Rib$^+$ and Rib$^-$), and the cells were then incubated at 37° C. with 5% CO$_2$ for 48 hours. Both transfected cell samples were homogenized and the cell lysates were extracted with Triton X-100. After the protein concentration was equalized in both samples, MAO B quantitation (by ELISA) and activity measurements were performed.
[1]Enzymatic activity μmol was expressed as μmol benzylamine/minute/mg MAO B.

As seen in FIG. 2, the percentage of MAO B activity obtained in cells grown in riboflavin-free medium, as compared to MAO B activity obtained in Rib$^+$ COS-7 cells, decreased with time in sequential experiments. However, MAO B expression levels (0.95±0.04 μg/mg protein) remained unchanged regardless of the extent of time the cells were grown in riboflavin-free medium. At a time interval of 100 days, the MAO B expressed in these cells had an activity of less than 5% of the MAO B holoenzyme activity obtained in transfected Rib$^+$ COS-7 cells. Thus, cells grown in riboflavin-free medium for greater than 100 days were defined as riboflavin-depleted COS-7 cells (Rib$^-$ COS-7 cells). Since MAO B was expressed in the absence of riboflavin and mammalian cells are incapable of synthesizing riboflavin, the MAO B expressed in Rib$^-$ COS-7 cells represents apo-MAO B. Rib$^-$ COS-7 cells were subsequently used for expression of apo-MAO B to examine flavin coupling.

EXAMPLE 14
Apo-MAO B can be inserted into the mitochondria

The distribution of protein, MAO B (apo- or holoenzyme), and MAO B activity in different subcellular compartments was shown in transfected Rib$^+$- and Rib$^-$ COS-7 cells by subcellular fractionation (TABLE II). The distribution of total protein in Rib$^+$- or Rib$^-$ COS-7 cells was essentially identical, with the largest amount of protein found in the cytosolic fraction. Approximately 80% of the holo- or apo-MAO B enzymes were found in the mitochondrial fraction of the Rib$^+$- or Rib$^-$ COS-7 cells, respectively. The activity of expressed holo- or apo-MAO B in various fractions was also determined. The activity distribution of holo-MAO B corresponded closely with the distribution of the enzyme, with the majority of activity (about 80%) located in the mitochondrial fraction. Although the total activity of apo-MAO B expressed in Rib$^-$ COS-7 cells was dramatically reduced, the small amount of remaining activity was also found mainly in the mitochondrial fraction (about 83%).

TABLE II

Comparison of protein, MAO B and activity distribution patterns between transfected Rib$^+$ and Rib$^-$ COS-7 cells

|  | Cell debris (P1) | Mitochondria (P2) | Microsome (P3) | Cytosol (S) |
|---|---|---|---|---|
| *Transfected Rib$^+$ COS-7 cells* | | | | |
| Protein (mg) | 0.05 (4.4%) | 0.18 (15.7%) | 0.28 (24.4%) | 0.64 (55.7%) |
| Holo-MAO B(ng) | 58 (6.1%) | 760 (79.3%) | 96 (10%) | 45 (4.7%) |
| Fraction activity (10$^{-4}$ mmol/minute) | 0.6 (4.5%) | 10.8 (83.3%) | 1.11 (8.6%) | 0.48 (3.7%) |
| *Transfected Rib$^-$ COS-7 cells* | | | | |
| Protein (mg) | 0.06 (5.4%) | 0.16 (14.4%) | 0.34 (30.6%) | 0.55 (49.5%) |
| Apo-MAO B(ng) | 101 (10.4%) | 800 (82.5%) | 66 (6.8%) | 3 (0.3%) |
| Fraction activity (10$^{-4}$ mmol/min) | 0.05 (6.1%) | 0.68 (82.9%) | 0.07 (8.5%) | 0.02 (2.4%) |

Transfected Rib$^+$ or Rib$^-$ COS-7 cells (1.2 × 10$^7$ cells) were fractionated by a modified method of Clark and Waterman (23). All fractions were assayed for: protein content by microBCA; holo-MAO B or apo-MAO B amount by ELISA; and MAO B activity using [$^{14}$C] benzylamine as substrate. The percentages of total amounts are shown in parentheses.

EXAMPLE 15
FAD coupling in intact cells

Figure 3:
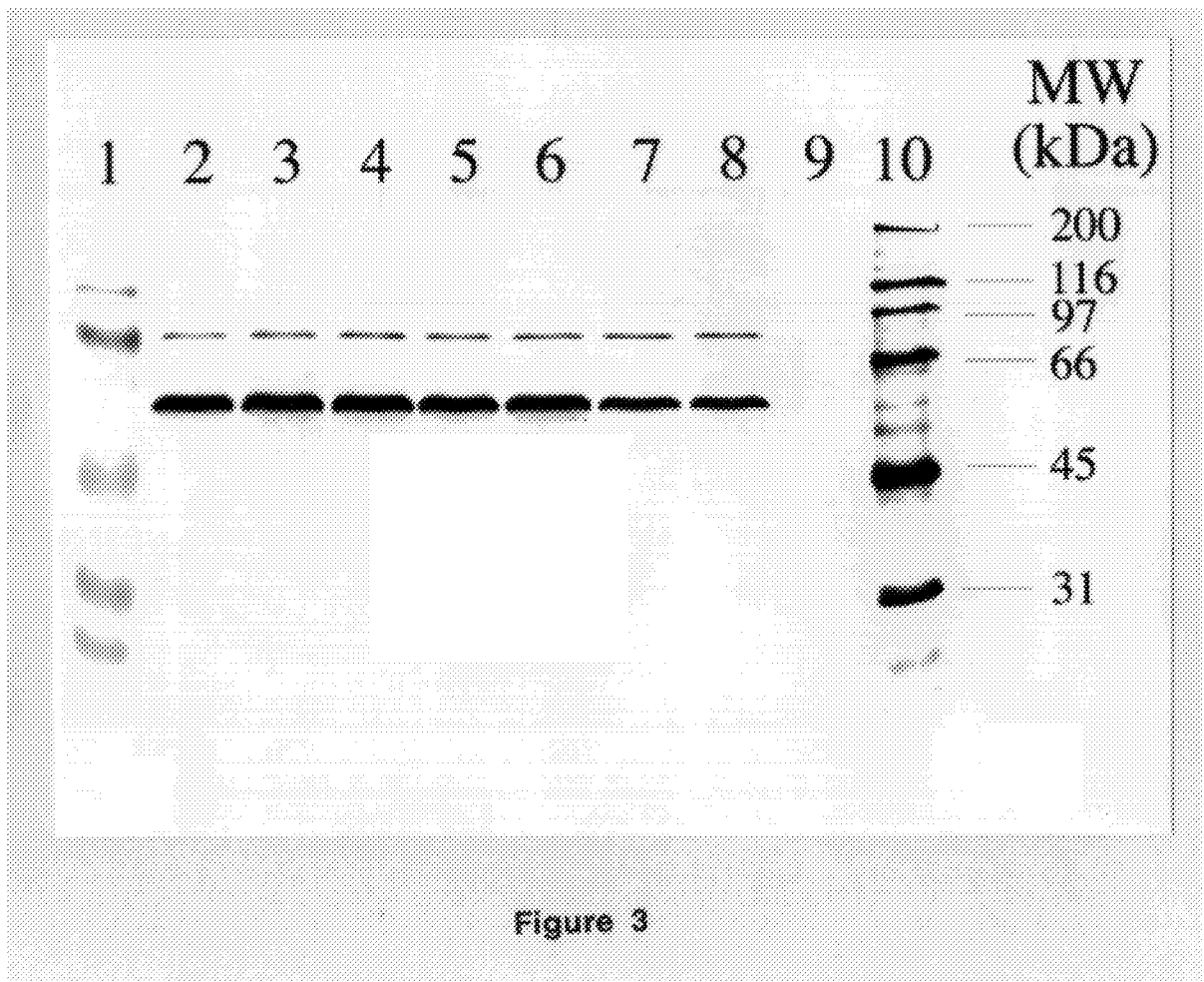
FIG. 3 shows a western blot analysis of MAO B cDNA transfected in Rib$^-$ COS-7 cells with the addition of different cofactors via electroporation. Expressed MAO B enzymes were adjusted to equal concentrations using ELISA before immunoprecipitation. Immunoprecipitated enzymes were separated on 10% SDS-PAGE, transferred to a nitrocellulose membrane and analyzed by Western blotting using the MAO B specific monoclonal antibody, MAO B-1C2. Lane 1: Prestained MW marker; Lane 2: MAO B obtained from transfected Rib$^+$ COS-7 cells, which served as a positive control. Lanes 3–8 contain MAO B obtained from transfected Rib$^-$ COS-7 cells with or without the addition of different cofactors. Lane 3: riboflavin; Lane 4: FMN; Lane 5: FAD; Lane 6: 8α-hydroxylriboflavin; Lane 7: NAD$^+$; Lane 8: no cofactor addition; Lane 9: untransfected Rib$^-$ COS-7 cells; Lane 10: Biotinylated MW marker.

When exogenous FAD was added simultaneously with MAO B cDNA in Rib$^-$ COS-7 cells during electroporation, restoration of MAO B activity was observed (TABLE III). Transfection of MAO B cDNA with exogenous FAD resulted in the recovery of 75% of MAO B holoenzyme activity, where MAO B holoenzyme activity refers to the enzymatic activity of MAO B holoenzyme expressed in Rib$^+$ COS-7 cells. Assuming that one mole of FAD binds to one mole of MAO B subunit, the amount of FAD (16 nmoles) used in the transfection was more than 500 fold the molar amount of expressed MAO B. A higher restoration of MAO B enzymatic activity could not be achieved by adding more exogenous FAD during electroporation. FMN or riboflavin were also capable of restoring approximately 75% of MAO B holoenzyme activity. However, only 40% of MAO B holoenzyme activity was obtained by the addition of 8α-hydroxyriboflavin. As expected, the addition of NAD$^+$ along with MAO B cDNA during electroporation did not yield active MAO B. Expressed MAO B enzymes (with or without cofactor additions) were further analyzed by Western blot using our MAO B specific monoclonal antibody, MAO B-1C2 (FIG. 3). A band at approximately 59 kDa was observed in all lanes that contained apo- or holo-MAO B.

TABLE III

Effect of adding different cofactors with MAO B cDNA into Rib$^-$ COS-7 cells via electroporation during the transfection process.

| Cofactor | MAO B Expressed | Enzymatic Activity$^1$ | Percent of Holo-MAO B Activity |
|---|---|---|---|
| Holo-MAO B$^2$ | 1.05 ± 0.25 | 1.13 ± 0.14 | 100 |
| Apo-MAO B$^3$ | 1.12 ± 0.04 | 0.02 ± 0.00 | 1.8 |
| Riboflavin | 0.90 ± 0.13 | 0.86 ± 0.06 | 76.1 |
| FMN | 0.81 ± 0.17 | 0.85 ± 0.03 | 75.2 |
| FAD | 0.86 ± 0.03 | 0.85 ± 0.01 | 75.2 |
| 8α-OH Rib | 0.95 ± 0.08 | 0.45 ± 0.01 | 39.8 |
| NAD$^+$ | 1.14 ± 0.06 | 0.02 ± 0.00 | 1.8 |

Various cofactors were added with MAO B cDNA into Rib$^-$ COS-7 cells via electroporation. After incubation at 37° C. with 5% CO$_2$ for 48 hours, transfected cells were harvested and MAO B concentration and activity were determined. Samples were run in duplicate in each experiment. Each value represents the mean ± SE from three separate experiments.
$^1$Enzymatic activity was expressed as μmol benzylamine/minute/mg MAO B.
$^2$Holo-MAO B was obtained by expressing MAO B cDNA in Rib$^+$ COS-7 cells, which served as a positive control.
$^3$Apo-MAO B was obtained by expressing MAO B cDNA in Rib$^-$ COS-7 cells without adding any cofactor.

EXAMPLE 16

FAD coupling in vitro

Figure 4:
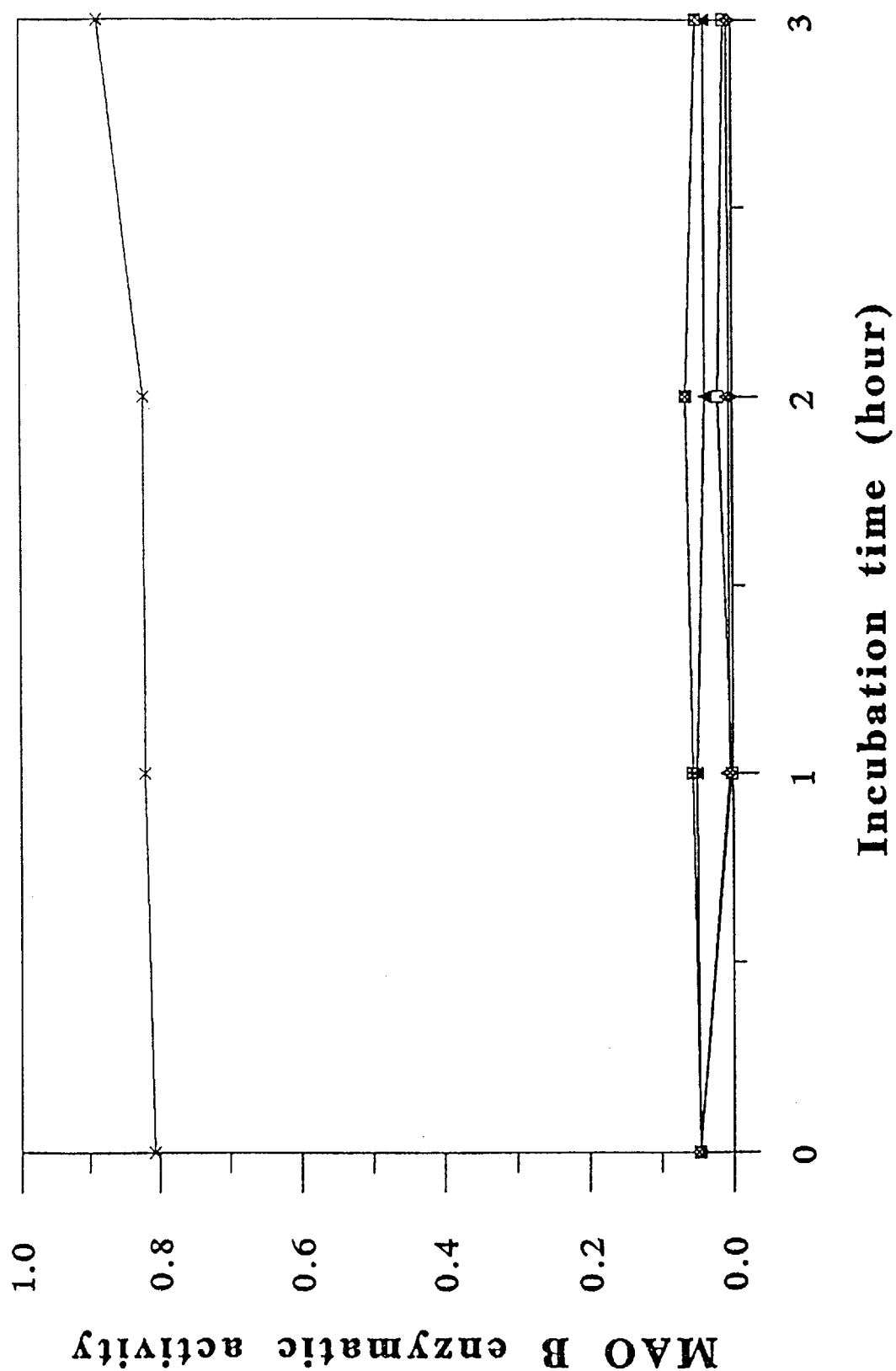
FIG. 4 shows in vitro flavinylation assays (see below). Triton extracted MAO B holoenzyme from a transfected Rib$^+$ COS-7 cell lysate, which served as a positive control, remained fully active during 3 hours incubation at 30° C. (- - - x - - - ). However, no MAO B catalytic activity was observed when FAD was added after apo-MAO B had been synthesized. Triton extracted (filled squares) or nonextracted (filled triangles) MAO B apoenzyme from transfected Rib$^-$ COS-7 cell lysate were incubated at 30° C. with exogenous FAD. Triton extracted MAO B apoenzyme from transfected Rib$^-$ COS-7 cell lysate were also incubated at 30° C. with exogenous FAD, an energy mixture and with or without 25% glycerol (filled diamonds: with glycerol; unfilled circles: without glycerol). The enzymatic activity of each sample was determined at 1 hour time intervals using [$^{14}$C] benzylamine as substrate.

Expressed MAO B holoenzyme, which served as a control, remained fully active in a cell lysate for up to 3 hours at 30° C. (FIG. 4). When exogenous FAD was added to Triton extracted or non-extracted lysates, which contained mitochondrial membrane-free or mitochondrial membrane-bound apo-MAO B, respectively, no MAO B catalytic activity was observed. Flavinylation of apo-MAO B in vitro was also attempted in the presence of an energy mixture and glycerol, but no MAO B activity was obtained.

EXAMPLE 17

Figure 5:
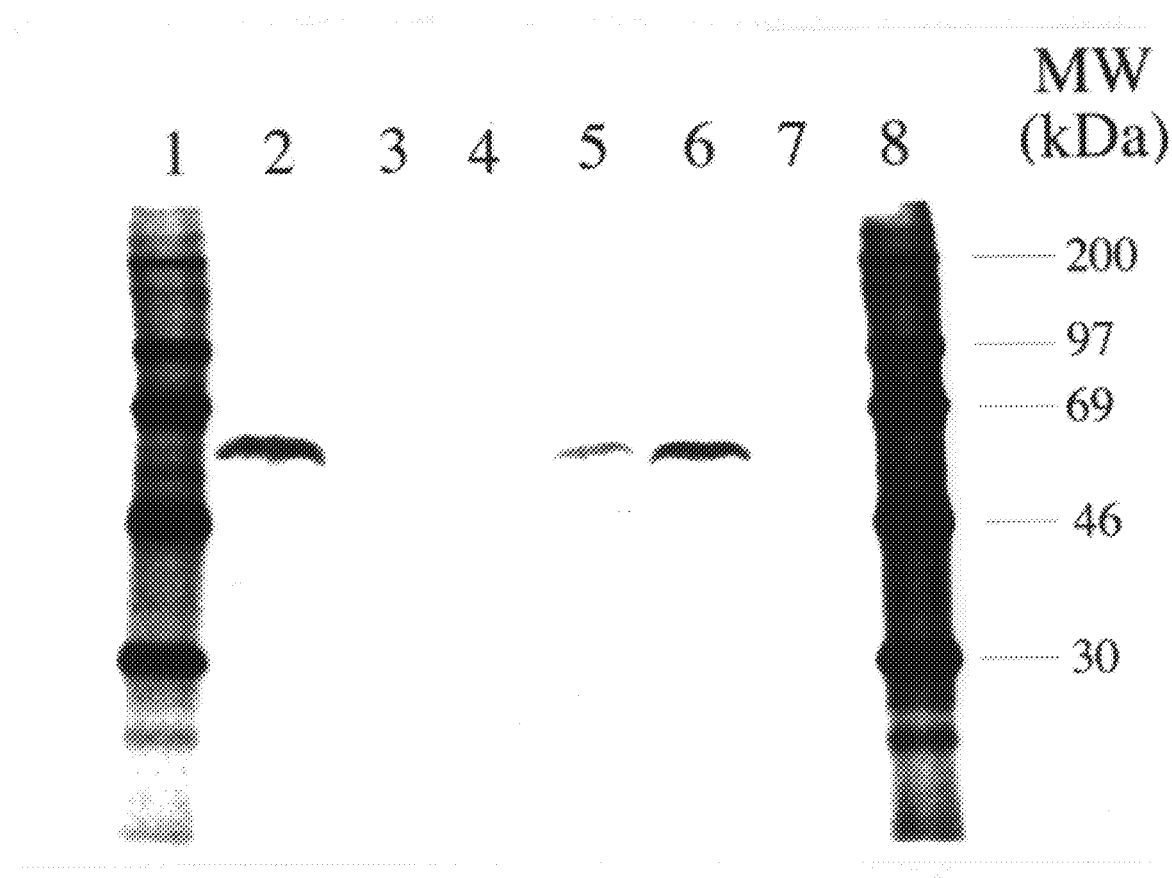
FIG. 5 shows an fluorography analysis of wild-type and mutant MAO B cDNAs which were transfected in Rib$^-$ COS-7 cells with the addition of exogenous [$^{14}$C] FAD. Expressed wild-type and variant MAO Bs were adjusted to equal concentrations using ELISA before immunoprecipitation. The immunoprecipitated enzymes were separated on 10% SDS-PAGE and analyzed on fluorography. Lane 1: [$^{14}$C] methylated MW marker; Lane 2: wild-type MAO B; Lane 3: E34A MAO B; Lane 4: E34Q MAO B; Lane 5: E34D MAO B; Lane 6: V10I MAO B; Lane 7: untransfected Rib$^-$ COS-7 cells; Lane 8: [$^{14}$C] methylated MW marker.

Glu$^{34}$ in the dinucleotide binding site of MAO B is required for FAD covalent binding To illustrate the role of Glu$^{34}$ in FAD binding, several mutant cDNAs to human MAO B in Rib$^+$ COS-7 cells (18) were constructed and transiently expressed. Mutation of the glutamate residue at position 34 in MAO B to glutamine (E34Q) or alanine (E34A) resulted in a complete loss of activity, and a mutation to aspartate (E34D) resulted in a 93% reduction in activity. The loss of activity was thought to be due to a loss of contact of the Glu$^{34}$ side chain with the ribose moiety of FAD. Whether the mutation resulted in misalignment of FAD at the noncovalent binding site or inability of the variant to covalently bind FAD remained unclear from activity measurements alone. However, coupling of FAD in wild-type or variant MAO B was directly assessed in the present invention by transfection of wild-type or mutant MAO B cDNAs and [$^{14}$C] FAD into Rib$^-$ COS-7 cells. The expressed wild-type and variant MAO Bs were adjusted to equal concentrations using ELISA before immunoprecipitation, and then analyzed by fluorography. The amount of incorporation of [$^{14}$C] FAD into MAO B enzymes was determined by the intensity of the bands at a molecular weight of about 59 kDa on the fluorogram (FIG. 5). The wild-type and the control variant (V10I) were each observed to have a dark band, which indicated that [$^{14}$C] FAD was incorporated into the enzyme. Variants E34A and E34Q did not exhibit bands, indicating that FAD was absent. A faint band was observed using a densitometer with variant E34D, indicating that a small amount of [$^{14}$C] FAD was incorporated (about 10 percent of wild-type). Thus, all variants of MAO B at residue 34 showed either a dramatic decrease or total loss of [$^{14}$C] FAD incorporation and a corresponding loss of enzymatic activity.

Flavinylation of MAO B has been difficult to study in the past, because FAD is covalently attached to Cys$^{397}$, and this cofactor cannot be removed without sacrificing MAO B activity (28). For mammalian flavoproteins, the conventional approach has been to study flavinylation in animals. Rabbits or mice were fed riboflavin-free diets to deplete the endogenous riboflavin, and the animals were sacrificed to obtain the organs or tissues for analysis (29). This method is time-consuming, tedious, and subject to variation due to individual differences in animals. The present invention provides a convenient and rapid method to manipulate flavinylation of eucaryotic proteins in Rib$^-$ COS-7 cells. Since COS-7 cells are not capable of synthesizing riboflavin, enzymes expressed in these cells lack flavin cofactors. As shown in FIG. 2, the relative percentage of MAO B enzymatic activity in sequential transfections decreased over time as COS-7 cells were grown in riboflavin-free medium. After 116 days, MAO B activity was nearly undetectable. The loss of MAO B activity was due to low concentrations of FAD as a result of riboflavin depletion in Rib$^-$ COS-7 cells. Thus, these cells were used to produce apo-MAO B to manipulate the steps involved in flavinylation. In other studies, Nishikimi et al. (30) produced the apoenzyme of L-gulono-g-lactone oxidase in a baculovirus expression system in which riboflavin levels were reduced. Enzymatic activity was observed upon addition of FAD, but no covalently bound FAD could be obtained using this system.

The expression level (0.95±0.04 μg/mg protein) of MAO B in transfected Rib$^-$COS-7 cells remained unchanged in sequential transfections during the process of riboflavin depletion (FIG. 2). This observation indicates that MAO B expression is not dependent upon riboflavin or FAD concentrations in the cell. The level of expressed MAO B was determined by ELISA, which is based upon epitope recognition by antibodies and is susceptible to major conformational changes. Both MAO B-1C2 monoclonal antibody and goat anti-MAO B polyclonal antibodies were capable of recognizing apo-MAO B. In another study, the apoenzyme of bacterial 6-hydroxy-D-nicotine oxidase, which contains covalently bound FAD in its holoenzyme, is not recognized by a molecular chaperone as aberrant (31). The conformation of the apo-MAO B, like apo-6-hydroxy-D-nicotine oxidase, may be similar to that of the native holoenzyme.

Mitoma and Ito (32) found that the mitochondria targeting sequence of MAO B is located on the C-terminus of the molecule. Deletion of the C-terminal 28 amino acids of MAO B abolished transfer of the enzyme to the mitochondria, while deletion of the N-terminal 55 amino acids had no effect on mitochondrial targeting. Furthermore, an expressed hybrid protein, in which the C-terminal 29 amino acids of MAO B was fused to the hydrophilic portion of cytochrome $b_5$, was localized in the mitochondria. The present invention demonstrated that apo-MAO B expressed in Rib⁻ COS-7 cells was localized in the mitochondrial fraction of cell lysates (Table 2), indicating that bound FAD was not necessary for MAO B insertion into the mitochondria membrane. These results are consistent with the notion that the target C-terminal sequence alone is sufficient for insertion into the membrane.

One advantage of using Rib⁻ COS-7 cells to manipulate flavinylation is that exogenous FAD or its derivatives can be introduced with MAO B cDNA into the cells during the transfection process. The enzymatic activity of MAO B with the addition of different flavins can be determined and compared with MAO B holoenzyme expressed in Rib⁺ COS-7 cells (Table 3). Addition of FAD resulted in the restoration of about 75% of holo-MAO B activity. Interestingly, approximately 75% of holo-MAO B activity was also achieved by the addition of riboflavin or FMN to transfected Rib⁻ COS-7 cells, suggesting the presence of abundant levels of cellular FAD synthetase. The addition of 8α-hydroxyriboflavin gave an enzyme with 40% activity of the control, which raises the possibility that this flavin may represent an intermediate in the activation of FAD (discussed below). Full recovery of MAO B enzymatic activity obtained in Rib⁺ COS-7 cells was not achieved for reasons that remain unknown. In other studies, however, Brandsch and Bichler (33) found that the covalent flavinylation of 6-hydroxy-D-nicotine oxidase in vitro required specific effectors (phosphorylated three carbon compounds), such as glycerol-3-phosphate, glyceraldehyde-3-phosphate or glycerate-3-phosphate. Effectors that could enhance the activity of MAO B have not been identified. It appears that the achievement of only 75% of activity may be due to a slight change in metabolism of Rib⁻ COS-7 cells which have been adapted to grow in riboflavin-free medium for more than 100 days.

Although it is known that FAD is covalently attached to active MAO B molecules, the form of the flavin which initially binds to MAO B in vivo has not previously been established. Theoretically, riboflavin or FMN could first bind to apo-MAO B followed by phosphorylation and adenylation, respectively, to form FAD. If riboflavin or FMN is the form that initially binds to apo-MAO B, one would expect FAD binding to be much less effective than riboflavin or FMN. Since MAO B activity was recovered to approximately the same extent (75%) using FAD, FMN or riboflavin, the flavin moiety which initially binds to apo-MAO B is apparently FAD. Apparently, FAD synthetase in these cells rapidly converted riboflavin and FMN to FAD by phosphorylation and adenylation, respectively, prior to incorporation. The presence of FAD was confirmed by measuring the covalent binding of [$^{14}$C] FAD to MAO B.

Figure 6:
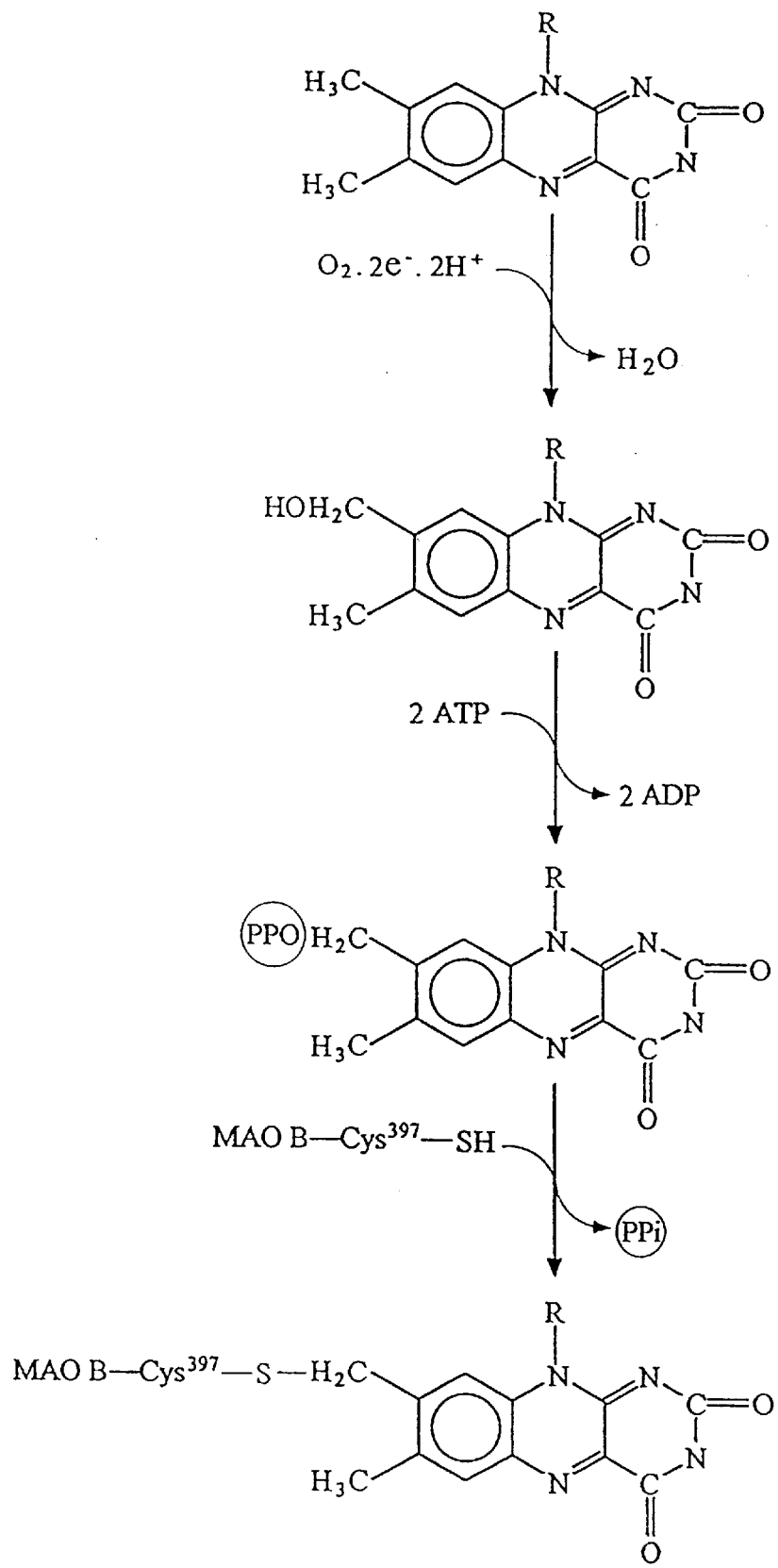
FIG. 6 shows a hypothetical mechanism of covalent bond formation postulated by Decker (11). This mechanism involves the enzymatic activation of the 8α-methyl group of the isoalloxazine ring of a flavin cofactor by hydroxylation and (pyro)phosphorylation, followed by covalent attachment to the apoenzyme (MAO B in this case).

The covalent attachment of FAD to Cys$^{397}$ could be autocatalytic, or catalyzed by an as yet uncharacterized enzyme. In either case, one of the participants, the 8α-methyl group of the flavin moiety or Cys$^{397}$ of MAO B, must be activated prior to coupling. Although the nucleophilicity of the Cys$^{397}$ residue may be influenced by surrounding amino acid residues, it is difficult to envision that a cysteine derivative would react with the inert 8α-methyl group of the flavin moiety. From a chemical point of view, activation of the 8α-methyl group appears essential for coupling of FAD to apo-MAO B. An enzymatically facilitated pathway for the incorporation of FAD into flavoproteins has been proposed by Decker (11) in which a flavin cofactor may be enzymatically activated by hydroxylation of the 8α-methyl group, followed by (pyro)phosphorylation (FIG. 6). Since the (pyro)phosphate is a good leaving group, a simple $S_N2$ reaction could facilitate the formation of the thioether between the flavin moiety and MAO B. Thus, the putative activated intermediate, 8α-hydroxyriboflavin was synthesized, and determined in Rib⁻ COS-7 cells its ability to generate MAO B enzymatic activity (synthesis of 8α-phosphate-riboflavin was also attempted, but was unsuccessful because the highly reactive hydroxyl groups on the ribityl moiety were also phosphorylated). If the flavin derivative is truly an intermediate, it would be capable of entering the flavinylation pathway to produce active MAO B. MAO B activity was obtained, but the level was only about one half of that obtained with the addition of riboflavin (Table 3). One possible explanation for the low activity is that a flavinylating enzyme binds the flavin substrate and catalyzes hydroxylation and phosphorylation sequentially without release of the 8α-hydroxy intermediate. Thus, the 8α-hydroxy intermediate may not be recognized as efficiently as riboflavin during the initial binding step. Alternatively, the covalent flavinylation of MAO B may be autocatalytic, since the unactivated form of the flavins (riboflavin, FMN and FAD) has higher effiency of incorporation into apo-MAO B than the putative activated form. Studies by Weyler et al. (34) support the concept that flavinylation of MAO may be autocatalytic, based on the observation that MAO expressed in yeast cells (*Saccharomyces cerevisiae*) is active and contains covalently bound FAD. Since yeast cells do not contain any known enzymes with covalently linked flavin, they reasoned that the cells are unlikely to contain any flavinylating enzymes which could have catalyzed the coupling reaction in MAO.

Studies were also conducted to determine whether flavinylation occurs as a co-translational or post-translational process. When FAD and MAO B cDNA were added simultanously to Rib⁻ COS-7 cells, active MAO B (containing FAD) was obtained. However, when FAD was added in vitro to whole cell lysates after apo-MAO B was synthesized, MAO B activity could not be regenerated (FIG. 4). Furthermore, when apo-MAO B was extracted from the mitochondrial membrane, attempts to regenerate active flavinylated MAO B were unsuccessful, even in the presence of various energy mixtures and glycerol (FIG. 4). The inability to couple FAD to apo-MAO B in vitro may indicate that flavinylation occurs as a cotranslational process during elongation of nascent chains to form functionally competent MAO B molecules.

Glu$^{34}$ in the dinucleotide binding motif is critical for MAO B catalytic activity (18). Two variants at Glu$^{34}$ (E34A and E34Q) were devoid of enzymatic activity, and another conservative variant, E34D, had only 7% of the wild-type activity. It was not known, however, whether the role of Glu$^{34}$ is confined to alignment of FAD for participation in the oxidation-reduction cycle of catalysis, or is involved in FAD incorporation. The present invention shows that the loss of activity in Glu$^{34}$ variants is linked to the inability to bind FAD covalently (FIG. 5).

Since FAD binds to two regions of MAO B (noncovalently at Glu$^{34}$ and covalently at Cys$^{397}$), the absence or low levels of FAD incorporation into Glu$^{34}$ variants reveals an important feature of the flavinylation process. If FAD coupling occurred by initial covalent attachment to Cys$^{397}$, Glu$^{34}$ variants would contain covalently bound FAD, but would be inactive because FAD could not interact properly at the dinucleotide binding site. Since little or no covalent binding of FAD was found in the Glu$^{34}$ variants, FAD apparently binds to Glu$^{34}$ first. Thus, the dinucleotide-binding site (including Glu$^{34}$) provides a topological dock for the initial binding of FAD and is instrumental in the delivery of FAD to Cys$^{397}$ in MAO B. The incoming flavin cofactor, which is initially bound to the dinucleotide binding site of MAO B, could be held for a finite time in a position which places the 8α-methyl group of FAD in exact and close proximity to Cys$^{397}$ to facilitate covalent flavinylation.

The dinucleotide-binding sites in various flavoproteins contain high sequence identity (17). However, the location within the primary structure varies from protein to protein, indicating that this site performs an autonomous function of cofactor-binding within a heterologous group of flavoproteins. Furthermore, in many flavoproteins containing dinucleotide-binding sites, FAD is not covalently bound (17). The present invention shows that the dinucleotide-binding site in MAO B plays a role in initial FAD binding and indicates that this site alone is sufficient for a flavoprotein to bind a flavin cofactor. The significance of covalent linkage between FAD and its flavoenzyme remains unresolved, but covalent binding could play a role in enzyme integrity and stability, substrate stereospecificity, cofactor economy, or redox potentials. Understanding the MAO flavinylation process may lead to the design of MAO enzymes with high redox potentials for better catalysis and to the rational design of MAO inhibitors. Since MAO inhibitors that covalently bind to FAD have long been the target of therapeutic drugs for the treatment of various psychiatric and neurological disorders, including depression (35) and Parkinson's disease (36), studies on flavinylation may lead to the development of therapeutic drugs that have high efficacy with minimal side effects.

The following references were cited herein:
1. Greenawalt, et al., (1970) *J. Cell. Biol.* 46, 173–179
2. White, et al., (1979) in *Monoamine Oxidase: Structure, Function, and Altered Functions*, pp. 129–144, Academic press, New York.
3. Johnston, J. P. (1968) *Biochem. Pharmacol.* 17, 1285–1297
4. Levitt, et al., (1982) *Proc. Natl. Acad. Sci.* 79, 6385–6389
5. Westlund, et al., (1985) *Science* 230, 181–183
6. Westlund, et al., (1988) *Neurosci.* 25, 439–456
7. Denney, et al., (1982) *Science* 215, 1400–1403
8. Denney, et al., (1982) *Mol. Pharmacol.* 24, 60–68
9. Kochersperger, et al., (1985) *J. Neurosci.* 11, 2874–2881
10. Bach, et al., (1988) *Proc. Natl. Acad. Sci.* 85, 4934–4938
11. Decker, K (1991) in *CRC Chemistry and Biochemistry of Flavoprotein*, Vol. II, (F. Muller ed.), pp. 343–375, CRC press.
12. Kearney, et al., (1971) *Eur. J. Biochem.* 24, 321–327
13. Walker, et al., (1971) *Eur. J. Biochem.* 24. 328–331
14. Gottowik, et al., (1993) *FEBS.* 317, 152–156
15. Wu, et al., (1993) *Mol. Pharmacol.* 43: 888–893
16. Wierenga, et al., (1986) *J. Mol. Biol.* 187, 101–107
17. Abell, et al., (1994) *Heterocycles* 39, 933–955
18. Kwan, et al., (1995) *Archs. Biochem. Biophys.* 316, 385–391
19. Singer, et al., (1955) *Arch. Biochem. Biophys.* 60, 255–257
20. Manstein, et al., (1986) *J. Biol. Chem.* 261, 16169–16173
21. McCormick, D. B. (1970) *J. Heterocycl. Chem.* 7, 447–450
22. Deng, et al., (1992) *Anal, Biochem.* 200, 81–88
23. Zimmerman, et al., (1982) *J. Membr. Biol.* 67, 165–182
24. Clark, et al., (1991) *J. Biol. Chem.* 266, 5898–5904
25. Yeomanson, et al., (1992) *Bioc. et Biophys. Acta* 1116, 261–268.
26. Wurtman, et al., (1963) *Biochem. Pharmacol.* 12, 1439–1440
27. Bonner, et al., (1974) *Eur. J. Biochem.* 46, 83–88
28. Watanable, et al., (1980) *B. B.R.C.* 94. 579–585
29. Dombrowski, et al., (1981) *Int. J. Biochem.* 13, 171–178
30. Nishikimi, et al., (1994) *Biochem. Mol. Biol. Intern.* 33, 313–320
31. Brandsch, et al., (1992) *J. Biol. Chem.* 267, 20844–20849
32. Mitoma, J-y., and Ito, A. (1992) *J. Biochem.* 111, 20–24
33. Brandsch, et al., (1989) *Eur. J. Biochem.* 182, 125–128
34. Weyler, et al., (1990) *B. B.R.C.* 173, 1205–1211
35. Da Prada, et al., (1989) *J. Neural. Transm.* 28, 5–20
36. Tetrud, J. W., and Langston, J. W. (1989) *Science* 245, 519–522

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of preparing apoenzyme of a riboflavin-dependent enzyme, comprising the steps of:
   growing COS-7 cells in a riboflavin-free medium;
   introducing a cDNA encoding a riboflavin-dependent enzyme; and
   expressing said cDNA.

2. The method of claim 1, wherein said enzyme is monoamine oxidase.

3. The method of claim 1, wherein said introduction is by transfection of the COS-7 cells with a cDNA encoding a riboflavin-dependent enzyme.

4. The method of claim 1, wherein said introducing is by electroporation.

* * * * *

UNITED STATES PATENT AND TRADEMARK OFFICE
CERTIFICATE OF CORRECTION

PATENT NO. : 5,863,776
DATED : January 26, 1999
INVENTOR(S) : Creed W. Abell, Sau-Wah Kwan, Binhua Zhou and Duane A.

It is certified that error appears in the above-identified patent and that said Letters Patent is hereby corrected as shown below:

Column 4,
Line 23, "an" should read -- a --.

Column 4,
Line 55, "that" should read -- than --.

Column 5,
Line 18, "methods" should read -- method --.

Column 8,
Line 44, "aliqout" should read -- aliquot --.

Signed and Sealed this

Eighteenth Day of September, 2001

Attest:

NICHOLAS P. GODICI
*Attesting Officer*   *Acting Director of the United States Patent and Trademark Office*